US012807555B2

(12) United States Patent
Hwang et al.

(10) Patent No.: US 12,807,555 B2
(45) Date of Patent: Nov. 24, 2026

(54) METHOD OF PREPARING ISOPROPYL ALCOHOL

(71) Applicant: LG CHEM, LTD., Seoul (KR)

(72) Inventors: Sung June Hwang, Daejeon (KR); Sung Kyu Lee, Daejeon (KR); Sung Kyun Kim, Daejeon (KR); Kyung Soo Jang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 446 days.

(21) Appl. No.: 18/707,415

(22) PCT Filed: Jun. 9, 2023

(86) PCT No.: PCT/KR2023/007922
§ 371 (c)(1),
(2) Date: May 3, 2024

(87) PCT Pub. No.: WO2024/039022
PCT Pub. Date: Feb. 22, 2024

(65) Prior Publication Data

US 2024/0417354 A1 Dec. 19, 2024

(30) Foreign Application Priority Data

Aug. 18, 2022 (KR) ........................ 10-2022-0103273
May 30, 2023 (KR) ........................ 10-2023-0069395

(51) Int. Cl.

| | |
|---|---|
| ***C07C 29/82*** | (2006.01) |
| ***B01D 3/14*** | (2006.01) |
| ***B01D 3/36*** | (2006.01) |
| ***C07C 29/04*** | (2006.01) |
| ***C07C 29/76*** | (2006.01) |
| ***C07C 29/80*** | (2006.01) |

(52) U.S. Cl.
CPC .............. *C07C 29/82* (2013.01); *B01D 3/141* (2013.01); *B01D 3/143* (2013.01); *B01D 3/36* (2013.01); *C07C 29/04* (2013.01); *C07C 29/76* (2013.01); *C07C 29/80* (2013.01)

(58) Field of Classification Search
CPC ................................ C07C 29/80; C07C 29/82
See application file for complete search history.

(56) References Cited

U.S. PATENT DOCUMENTS

| | | | |
|---|---|---|---|
| 2016/0207858 | A1 | 7/2016 | Park et al. |
| 2021/0061741 | A1 | 3/2021 | Kim et al. |

FOREIGN PATENT DOCUMENTS

| | | | |
|---|---|---|---|
| CN | 105712839 | A | 6/2016 |
| CN | 106631697 | A | 5/2017 |
| JP | 2016-531130 | A | 10/2016 |
| KR | 1999-014837 | A | 2/1999 |
| KR | 10-2004-0085710 | A | 10/2004 |
| KR | 10-0790413 | B1 | 1/2008 |
| KR | 10-1662896 | B1 | 10/2016 |
| KR | 10-2020-0065579 | A | 6/2020 |

(Continued)

*Primary Examiner* — Medhanit W Bahta
(74) *Attorney, Agent, or Firm* — Bryan Cave Leighton Paisner LLP

(57) ABSTRACT

Provided is a method of preparing isopropyl alcohol (IPA) including a purification step using a plurality of column, the method allows recovery of IPA with high purity, by separating water first before removing NPA and applying a dividing wall column (DWC) to perform both separation of IPA and NPA and separation of water and high-boiling point organic substances.

9 Claims, 2 Drawing Sheets

(56) References Cited

FOREIGN PATENT DOCUMENTS

| | | | |
|---|---|---|---|
| KR | 10-2021-0035735 | A | 4/2021 |
| KR | 10-2021-0158146 | A | 12/2021 |
| KR | 10-2015-0021483 | A | 3/2025 |
| WO | 2018-135408 | A1 | 7/2018 |
| WO | 2020-111439 | A1 | 6/2020 |

【FIG. 1】
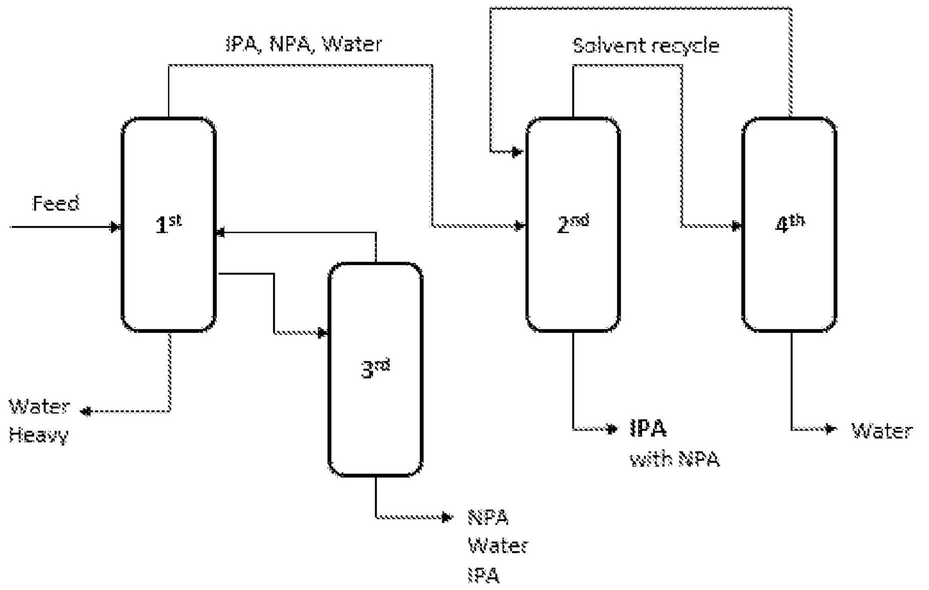
【FIG. 2】
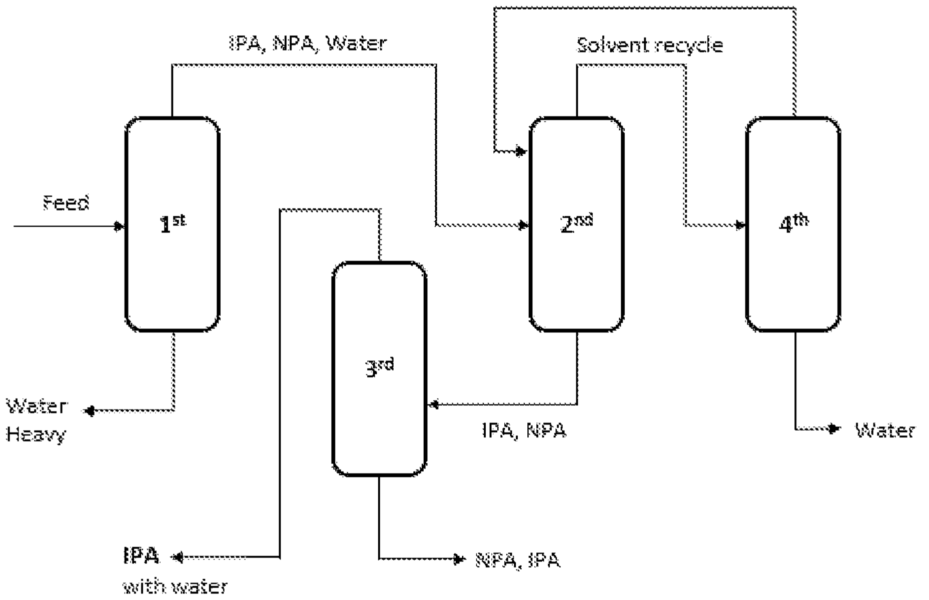

【FIG. 3】
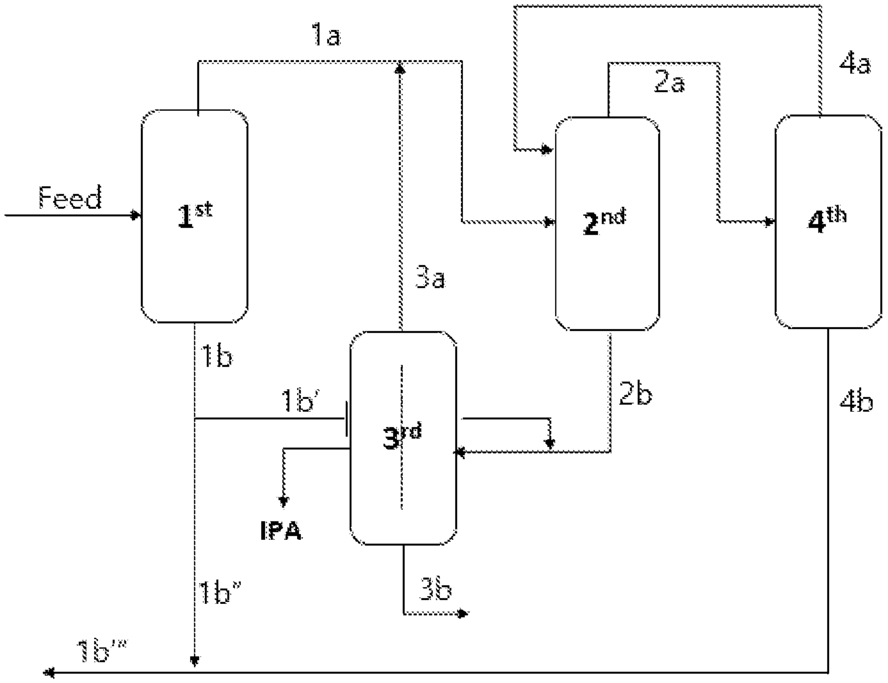

METHOD OF PREPARING ISOPROPYL ALCOHOL

CROSS-REFERENCE TO RELATED APPLICATIONS

This application is a National Stage Application of International Application No. PCT/KR2023/007922 filed on Jun. 9, 2023, and claims the benefit of priorities to Korean Patent Application No. 10-2022-0103273, filed on Aug. 18, 2022, and Korean Patent Application No. 10-2023-0069395, filed on May 30, 2023, the disclosures of which are incorporated herein by reference in their entirety.

FIELD

The present disclosure relates to a method of preparing isopropyl alcohol, and more particularly, to a method of purifying isopropyl alcohol to high purity from a reaction product.

BACKGROUND

Isopropyl alcohol (IPA) is used for various purposes including a solvent for cleaning agents, raw materials for industrial paints and reagents, paints, inks, and the like in the electronics industry such as manufacture of semiconductor or liquid crystal display (LCD).

IPA may be prepared by reacting propylene and water. For example, a propylene monomer and water are reacted in a reactor to obtain a reaction product including IPA, an unreacted propylene monomer, unreacted water, n-propyl alcohol (NPA), by-products such as low-boiling point organic substances or high-boiling point organic substances, and the like, and the reaction product is transferred to a gas purification unit, in which low-boiling point substances (including unreacted propylene monomer) is discharged from the upper portion and a stream including IPA, NPA, and water is separated to the lower portion, and the lower stream (including IPA, NPA, water, and high-boiling point organic substances) is transferred to an IPA purification unit including a plurality of columns in which IPA is separated. The unreacted propylene monomer and the unreacted water may be recovered and used in an IPA preparation process.

FIGS. 1 and 2 schematically show an IPA purification process performed in the method of preparing IPA of the conventional art.

First, referring to FIG. 1, a feed stream including IPA, NPA, water, and high-boiling point organic substances is supplied to a first column of a purification unit, a stream including water and high-boiling point organic substances is discharged to the lower portion, a stream including IPA, NPA, and an azeotropic mixture of water is separated into the upper portion and transferred to a second column, and NPA is removed from the lower portion of a third column connected to the side portion of the first column. Subsequently, the azeotropy is broken using a solvent in the second column, a lower stream including IPA and an upper stream including the organic solvent and water are separated, and the used solvent and water are separated in a fourth column. That is, in the IPA purification process of FIG. 1, NPA is first removed and then water is separated.

The first column and the third column include a large amount of water, and since the azeotropic point of IPA and water at normal pressure is 80.4 °C and the azeotropic point of NPA and water is 87.7 °C, azeotropic mixtures of water/IPA and water/NPA are formed. Therefore, even though NPA is removed from the lower portion of the third column, NPA is included in the stream transferred to the second column, and thus, NPA remains when finally recovering IPA, so that production of high-purity IPA is difficult.

In order to overcome this, in Korean Patent Laid-Open Publication No. 10-2020-0065579, water is first separated before removing NPA in the IPA purification process, thereby producing high-purity IPA.

Specifically, referring to FIG. 2, a feed stream is separated into an upper stream including an azeotropic mixture of IPA, NPA, and water and a lower stream including high-boiling point organic substances and water in a first column of a purification unit, the upper stream is transferred to a second column to separate water first, and a stream including IPA and NPA is transferred to a third column to remove NPA, thereby recovering IPA. That is, since in the IPA purification process of FIG. 2, water is first separated from the azeotropic mixture of IPA, NPA, and water in the second column, the azeotropic mixture is not formed in the third column, so that NPA is easily removed, and as a result, NPA remaining in finally recovered IPA is less than that in the purification of FIG. 1, but water which is not separated in the second column may be included in the final IPA recovery.

In addition, in the conventional IPA purification process as in FIGS. 1 and 2, since high-boiling point organic substances (heavy substances) are included in water discharged to the lower portion of the first column, the chemical oxygen demand (COD) of the discharged water is increased and an additional process may be required for a process water or wastewater treatment.

SUMMARY

In order to solve the problem of the conventional method that NPA is not effectively removed and the COD of water treated as process water or wastewater is high because water forms an azeotrope with each of IPA and NPA, an object of the present disclosure is to provide a preparation method which allows recovery of isopropyl alcohol with high purity, by changing a purification order to separate water first before removing NPA and applying a dividing wall column (DWC) to perform both separation of IPA and NPA and separation of water and high-boiling point organic substances.

In one general aspect of the present disclosure, a method of preparing isopropyl alcohol (IPA) includes:

(S1) performing gas purification to separate gas from a reaction product of a propylene monomer and water to obtain a feed stream including IPA, NPA, water, and high-boiling point organic substances; and (S2) supplying the feed stream to a purification unit including a plurality of columns to recover IPA, wherein in a first column of the purification unit, the feed stream is separated into an upper stream including IPA, NPA, and water and a lower stream including water and high-boiling point organic substances, wherein, in a second column of the purification unit, water is removed from the upper stream of the first column using an organic solvent, a stream including IPA and NPA is separated to a lower portion, and the organic solvent forms a three-component azeotropic mixture with water and IPA, which is discharged as an upper stream, wherein a third column of the purification unit includes first and second areas which are separated by a center dividing wall, a mixed stream of a branch stream of the lower stream of the first column and the lower stream of the second column is supplied to the first area, where the mixed stream is separated into an upper stream including water from which the high-boiling point organic substances have been removed, a side stream including IPA from which NPA has been removed, and a lower stream including the high-boiling point organic substances and NPA, and the side stream including IPA is recovered from the second area.

According to the present disclosure, in the preparation of IPA, water is first separated from a feed stream including IPA, NPA, water, and high molecular organic substances in a purification step using a plurality of columns, and then a mixed stream of a branch stream of a lower stream (including water and high-boiling point organic substances) of the first column and a lower stream (including IPA and NPA) of a second column is supplied to a first area of a third column, which corresponds to a dividing wall column, to separate the high-boiling point organic substances and NPA. Thereby, a high-purity of IPA from which NPA has been removed can be recovered to a side of a second area of the third column, while water from which the high-boiling point organic substances have been removed can be discharged as an upper stream of the third column.

IPA recovered to the second area of the third column, which corresponds to a dividing wall column, may be 99.99% or more of IPA included in the feed.

In addition, in the third column, which corresponds to a dividing wall column, water included in a branch stream of the lower stream of the first column is separated from the high-boiling point organic substances and refluxed. Thereby, water being remained in the lower stream of the first column is combined with a portion of the lower portion of the fourth column, followed by recycling as process water or treating as wastewater having a lowered chemical oxygen demand (COD).

BRIEF DESCRIPTION OF DRAWINGS

FIGS. 1 and 2 schematically show IPA purification processes performed in a method of preparing IPA of the conventional art, respectively.

FIG. 3 schematically shows an IPA purification process performed in a method of preparing IPA according to an exemplary embodiment of the present disclosure.

DETAILED DESCRIPTION

The terms and words used in the description and claims of the present disclosure are not to be construed limitedly as having general or dictionary meanings but are to be construed as having meanings and concepts meeting the technical ideas of the present disclosure, based on a principle that the inventors are able to appropriately define the concepts of terms in order to describe their own inventions in the best mode.

The meaning of "comprising" or "containing" used herein embodies specific characteristics, domains, integers, steps, actions, elements, or components, and does not exclude the addition of other specific characteristics, domains, integers, steps, actions, elements, or components.

The term "stream" used herein may refer to a fluid flow in a process, or may refer to a fluid itself flowing in a pipe. Specifically, the stream may refer to both a fluid itself flowing in a pipe connecting each device and a fluid flow. In addition, the fluid may include any one or more components of gas, liquid, and solid.

The term "upper portion" used herein refers to, unless otherwise stated, a point of a height from 0 to 20% from the top to the bottom of an apparatus, and specifically, may refer to a top (tower top). In addition, the term "lower" refers to a point of a height from 80 to 100% from the top to the bottom of an apparatus, and specifically, may refer to a bottom (tower bottom).

The term "side stream" used herein refers to, unless otherwise stated, a stream discharged from a height from 25 to 80% or discharged from a height from 40 to 70% from the top to the bottom of an apparatus.

In addition, "pressure" mentioned herein refers to gauge pressure measured based on atmospheric pressure.

An exemplary embodiment of the present disclosure relates to a method of preparing isopropyl alcohol (IPA), and specifically, includes an obtaining step of a feed stream (S1) and a purification step of recovering IPA from the feed stream (S2).

Hereinafter, the method of preparing IPA according to an exemplary embodiment of the present disclosure will be described in detail step by step.

In step (S1) of the method of preparing IPA according to the present disclosure, gas purification is performed from a reaction product of a propylene monomer and water to obtain a feed stream including IPA, NPA, water, and high-boiling point organic substances.

Specifically, the feed stream may be obtained by reacting a propylene monomer and water in a reactor to produce a reaction product including IPA, an unreacted propylene monomer, unreacted water, and as by-products, n-propyl alcohol (NPA), low-boiling point organic substances, and high-boiling point organic substances, and performing gas purification of separating low-boiling point components including the unreacted propylene monomer from the reaction product.

In the reactor, propylene and water may be performed in any one form of a gaseous reaction, a gas/liquid reaction, or a liquid reaction, and a mole ratio of water to the propylene monomer may be from 0.3 to 2 or from 0.35 to 1.5. When the mole ratio is satisfied, a forward reaction of an equilibrium reaction is promoted and a reverse reaction is prevented from proceeding, thereby increasing the yield of IPA.

In addition, the reactor may be operated in optimal conditions in which IPA may be efficiently prepared by a reaction of a propylene monomer and water, and for example, a gaseous reaction may be operated at a pressure of 10 to 50 $kg/cm^2{\cdot}g$, 30 to 50 $kg/cm^2{\cdot}g$, or 35 to 45 $kg/cm^2{\cdot}g$ and a temperature of 150 to 220 °C, 160 to 220 °C, or 180 to 215 °C.

The reaction product may include an unreacted propylene monomer, unreacted water, and as by-products, n-propyl alcohol (NPA), isopropyl ether (DIPE), heavy high-boiling point organic substances (for example, hexanol), and additionally low-boiling point organic substances (for example, acetone), and the like, in addition to IPA. Therefore, in order to obtain IPA in high purity, a process of separating an unreacted material and by-products included in a reaction product and recovering IPA is needed. In addition, water separated from the reaction product may be recovered, and recycled as process water or treated as wastewater. If the water includes heavy high-boiling point organic substances, a chemical oxygen demand (COD) may be increased. Accordingly, a process of decreasing COD during wastewater treatment may be required.

To this end, the reaction product is first subjected to gas purification and then supplied to an IPA purification unit. The gas purification is for removing low-boiling point components including an unreacted propylene monomer from the reaction product, and may be performed using an absorption column, a gas purification unit, and the like.

In step (S2) of the method of preparing IPA according to the present disclosure, IPA is purified from a stream including IPA, NPA, water, and heavy high-boiling point organic substances, and the purification of IPA may be performed in a purification unit including a plurality of columns as shown in FIG. 3.

Referring to FIG. 3, a feed stream obtained in step (S1) is supplied to a first column of the purification unit. The feed stream may include 5 to 10 wt % of IPA, 0.1 to 3 wt % of NPA, 85 to 94 wt % of water, and 0.05 to 2 wt % of high-boiling point organic substances.

The first column of the purification unit corresponds to a distillation column for separating a large amount of water included in the feed and separating IPA and NPA to the upper portion, IPA and NPA form azeotropic mixtures with water, respectively and separated to the upper stream 1*a*, and high-boiling point organic substances are discharged to the lower stream 1*b* with water.

The upper discharge stream 1*a* from the first column may include a mixture of 30 to 70 wt % of IPA, 20 to 50 wt % of NPA, and 10 to 50 wt % of water, and the lower discharge stream 1*b* from the first column may include 95 to 99 wt % of water and 1 to 5 wt % of high-boiling point by-products.

The first column may be operated at a pressure of 0 to 3 $kg/cm^2 \cdot g$ or 0 to 2 $kg/cm^2 \cdot g$ and a temperature of 80 to 150 °C or 90 to 140 °C for increasing the separation efficiency of an alcohol component and water from the reaction product.

The first column is for separating water from IPA and NPA, but it is difficult to completely remove water due to formation of azeotrope with water. Thus, in order to completely separate water from the azeotropic mixture included in the upper stream 1*a* of the first column, the stream 1*a* is transferred to a second column.

That is, the second column of the purification unit is for separating water from a stream including IPA, NPA, and water, specifically a stream 1*a* including an azeotropic mixture of IPA/water and an azeotropic mixture of NPA/water, and when an organic solvent (for example, cyclohexane, benzene, toluene, isopropyl acetate, and the like) is added as an azeotropic agent, azeotropy of IPA or NPA and water is broken to separate water. Therefore, in the second column, water is removed and a stream 2*b* including IPA and NPA is separated to the lower portion, and the organic solvent forms a three-component azeotropic mixture with water and IPA and discharged to an upper stream 2*a.*

When cyclohexane is used as the azeotropic agent, the upper stream 2*a* of the second column may include an azeotropic mixture of 65 to 85 wt % of an organic solvent, 4 to 15 wt % of water, and 10 to 30 wt % of IPA.

The second column may be operated at a pressure of 0 to 2 $kg/cm^2 \cdot g$ or 0 to 1 $kg/cm^2 \cdot g$ and a temperature of 50 to 110 °C or 60° to 100° for increasing the separation efficiency of water by the organic solvent used as the azeotropic agent.

The lower stream 2*b* of the second column may include 70 to 98 wt % of IPA and 2 to 30 wt % of NPA, and further, a small amount of water which is not separated in the previous step may remain, and the stream 2*b* is transferred to a third column for recovering IPA.

The third column corresponds to a dividing wall distillation column (DWC) including two areas divided by a center dividing wall, as illustrated in FIG. 3, and a lower stream 2*b* of the second column is supplied to one of the areas (first area). Herein, a branch stream 1*b*' of a stream 1*b* which is separated from the lower portion of the first column and includes water and high-boiling point organic substances may be mixed with the lower stream 2*b* of the second column, and the mixed stream may be supplied to the first area of the third column together.

The third column separates high-boiling point organic substances and NPA having a high boiling point to a lower stream 3*b* from the mixed stream, thereby obtaining an upper stream 3*a* including water from which high-boiling point organic substances have been removed and a side stream including IPA from which NPA has been removed. The side stream including IPA from which NPA has been removed is recovered in another area of the third column (second area), thereby purifying 99.99 wt % or more of IPA included in the feed.

In the upper stream 3*a* of the third column, water from which high-boiling point organic substances have been removed forms an azeotropic mixture with IPA and is discharged, the stream 3*a* is mixed with the upper stream 1*a* including the azeotropic mixtures of IPA/water and NPA/water of the first column and transferred to the second column, and in the second column, water may be separated from the azeotropic mixture. In addition, the separated water may be discharged to the lower portion of the fourth column.

As such, since water included in a portion of the lower stream of the first column is separated from the high-boiling point organic substances and refluxed in the third column, water 1*b*" remaining in the lower stream of the first column may be combined with a stream 4*b* separated in the lower portion of the fourth column and discharged to water 1*b*''', which may be recycled as process water and treated as wastewater having a lowered chemical oxygen demand (COD).

In an exemplary embodiment of the present disclosure, the content of the high-boiling point organic substances separated into the lower stream of the third column may be proportional to the flow rate of the branch stream of the lower stream of the first column supplied to the first area of the third column, but considering the economical aspect of energy consumption, appropriate control is needed. For example, a branch stream 1*b*' of the lower stream of the first column supplied to the first area of the third column may be branched at a flow rate of 0.5 to 5 wt % or 1 to 3 wt % of the total flow rate of the lower stream of the first column, and when the flow rate of the branch stream is less than 0.5 wt %, the removal rate of the high-boiling point organic substances is low, so that a COD reduction effect is insufficient. When the flow rate of the branch stream is more than 5 wt %, excessive energy consumption may be induced in the third column.

In addition, in order to increase separation efficiency of the high-boiling point organic substances and NPA from the mixed stream, the third column may be separated at a pressure of 0 to 2 $kg/cm^2 \cdot g$ or 0 to 1 $kg/cm^2 \cdot g$ and a temperature of 70 to 120 °C or 80 to 110 °C.

Meanwhile, the upper stream including the organic solvent and water separated in the upper portion of the second column is transferred to a fourth column of the purification unit for recovering the organic solvent and may be separated into an upper stream 4*a* from which water has been removed and a lower stream 4*b* including water, and the organic solvent included in the upper stream 4*a* may be refluxed to the second column.

The fourth column is a solvent recovery column, and in order to increase separation efficiency of the organic solvent and water, may be operated at a pressure of 0 to 2 kg/cm$^2$·g or 0 to 1 kg/cm$^2$·g and temperature of 70 to 120 °C or 75 to 110 °C.

According to the present disclosure as described above, in the preparation of IPA, water is first separated from a feed stream including IPA, NPA, water, and high molecular organic substances in a purification step using a plurality of columns, and then a mixed stream of a branch stream of a lower stream (including water and high-boiling point organic substances) of the first column and a lower stream (including IPA and NPA) of a second column is supplied to a first area of a third column, which corresponds to a dividing wall column, to separate the high-boiling point organic substances and NPA. Thereby, a high-purity of IPA from which NPA has been removed can be recovered to a side of a second area of the third column, while water from which the high-boiling point organic substances have been removed can be discharged as an upper stream of the third column.

IPA which is recovered to the second area of the third column, which corresponds to a dividing wall column, may account for 99.99 wt % or more of IPA included in the feed.

In addition, in the third column, which corresponds to a dividing wall column, water included in a branch stream of the lower stream of the first column is separated from the high-boiling point organic substances and refluxed, whereby water which is discharged after water remaining in the lower stream of the first column and a portion of the stream separated from the lower portion of the fourth column are combined may be recycled as process water or treated as wastewater having a lowered chemical oxygen demand (COD).

EXAMPLES AND COMPARATIVE EXAMPLES

Hereinafter, the present disclosure will be described in more detail by the examples. However, the following examples are provided for illustrating the present disclosure, and it is apparent to a person skilled in the art that various modifications and alterations may be made without departing from the scope and spirit of the present disclosure and the scope of the present disclosure is not limited thereto.

Example 1

(Step 1) Obtaining of Feed Stream

A propylene monomer and water were reacted in a gas phase at a mole ratio of 1:1 to produce a reaction product including isopropyl alcohol (IPA), an unreacted propylene monomer, unreacted water, and as by-products, n-propyl alcohol (NPA), low-boiling point organic substances, and high-boiling point organic substances, and then a purification process to separate low-boiling point components including the unreacted propylene monomer and gas components from the reaction product was performed to obtain a feed stream. The feed stream included 7 wt % of IPA, 0.2 wt % of NPA, 92.7 wt % of water, and 0.1 wt % of high-boiling point organic substances.

(Step 2) Purification of Isopropyl Alcohol (IPA)

As shown in FIG. 3, the feed stream obtained in step 1 was supplied to the purification unit including first to fourth columns to recover IPA.

First, the feed stream was supplied to the first column, and the first column was operated at 0 kg/cm$^2$·g at 90 °C in the upper portion and at 140 °C in the lower portion to separate the feed stream into an upper stream 1*a* including IPA, NPA, and water and a lower stream 1*b* including water and high-boiling point organic substances.

The upper stream 1*a* and an organic solvent (cyclohexane) as an azeotropic agent were supplied to the second column, and the second column was operated at 0 kg/cm$^2$·g at 60 °C in the upper portion and at 100 °C in the lower portion to remove water from the stream 1*a* and separate a stream 2*b* including IPA and NPA to the lower portion, while a stream including an azeotropic mixture of the organic solvent, water, and IPA was discharged to the upper portion.

Thereafter, the lower stream 2*b* of the second column and a branch stream 1*b*' of the lower stream 1*b* of the first column were mixed and supplied to the first area of the third column, which corresponds to a dividing wall column. At this time, the flow rate of the branch stream 1*b*' was adjusted to 0.5 wt % of the total flow rate of the lower stream of the first column.

The third column was operated at 0 kg/cm$^2$·g at 80 °C in the upper portion and at 110 °C in the lower portion to separates high-boiling point organic substances and NPA having a high boiling point to a lower stream 3*b* from the mixed stream, thereby obtaining an upper stream 3*a* including water from which high-boiling point organic substances had been removed and a side stream including IPA from which NPA has been removed. The side stream including IPA from which NPA had been removed was recovered from the second area of the third column, thereby purifying IPA included in the feed in a purity of 99.99 wt % or more.

Meanwhile, the upper stream (including the organic solvent and water) of the second column was transferred to the fourth column, the fourth column was operated at 0 kg/cm$^2$·g at 75 °C in the upper portion and at 100 °C in the lower portion to separate the stream into an upper stream 4*a* from which water had been removed and a lower stream 4*b* including water, and the organic solvent included in the upper stream 4*a* was refluxed to the second column. In addition, water 1*b*" remaining in the lower stream of the first column was combined with the stream 4*b* separated from the lower portion of the fourth column and discharged.

Example 2

IPA was recovered in the same manner as in Example 1, except that the flow rate of the branch stream 1*b*' from the lower portion of the first column supplied to the first area of the third column was adjusted to 5 wt % of the total flow rate of the lower stream of the first column.

Example 3

IPA was recovered in the same manner as in Example 1, except that the flow rate of the branch stream 1*b*' from the lower portion of the first column supplied to the first area of the third column was adjusted to 10 wt % of the total flow rate of the lower stream of the first column.

Comparative Example 1

(Step 1)

A feed stream was obtained in the same manner as in step 1 of Example 1.

(Step 2)

The purification process as shown in FIG. 1 was performed.

Specifically, a feed stream was supplied to the first column to separate the stream into an upper stream including an azeotropic mixture of IPA, NPA, and water and a lower stream including water and high-boiling point organic substances. The upper stream of the first column was transferred to the second column, while NPA was removed to the lower portion of the third column connected to the side of the first column. Subsequently, the azeotropy was broken using an organic solvent (cyclohexane) in the second column, a lower stream including IPA and an upper stream including the organic solvent and water were separated, and the used solvent and water were separated in a fourth column.

Comparative Example 2

(Step 1)

A feed stream was obtained in the same manner as in step 1 of Example 1.

(Step 2)

The purification process as shown in FIG. 2 was performed.

Specifically, a feed stream was supplied to the first column to separate the stream into an upper stream including an azeotropic mixture of IPA, NPA, and water and a lower stream including high-boiling point organic substances and water. The upper stream from the first column was transferred to the second column to separate water first, and then a stream including IPA and NPA was transferred to the third column to remove NPA, thereby recovering IPA. Meanwhile, the used solvent and water were separated in the fourth column. The following Table 1 shows the results of recovering IPA according to the purification processes of the examples and the comparative examples.

the chemical oxygen demand (COD) was the highest and as a result, an additional process may be required in treating wastewater.

In Comparative Example 2, since water was first separated from an azeotropic mixture of IPA, NPA, and water in the second column during IPA purification, the azeotropic mixture was not formed in the third column, so that NPA was easily removed, and as a result, finally recovered IPA had remaining NPA as low as 2 ppm. However, water which was not separated yet was included at a concentration of 50 ppm in the second column during the final IPA recovery. In addition, similar to Comparative Example 1, since high-boiling point organic substances (heavy substances) were included in water discharged to the lower portion of the first column, the chemical oxygen demand (COD) was high.

However, in Examples 1 to 3, the third column, which is a dividing wall column, was used to first separate water from a stream including azeotropic mixtures of IPA/water and NPA/water, and then a mixed stream of the branch stream 1*b*' of the lower stream (including water and high-boiling point organic substances) of the first column and the lower stream 2*b* (including IPA and NPA) of the second column was supplied to the first area of the third column, which is a dividing wall column, to remove the high-boiling point organic substances and NPA, and as a result, high-purity IPA from which NPA had been removed was recovered and the concentrations of remaining NPA and remaining water were as low as 2 ppm and 10 ppm, respectively.

Furthermore, in Examples 1 to 3, water included in the lower branch stream 1*b*' of the first column was separated

TABLE 1

| | Purification order of IPA | Flow rate of branch stream based on the total flow rate of lower stream of first column | Final IPA recovery results: Purity (wt %) | NPA concentration (ppm) | Water concentration (ppm) | Waste water COD [1] | Amount of steam used [2] |
|---|---|---|---|---|---|---|---|
| Comparative Example 1 | Separation of water after removing NPA | — | 99.92 | 500 | 250 | 1 | 1 |
| Comparative Example 2 | Removal of NPA after separating water | — | 99.995 | 2 | 50 | 1 | 1.06 |
| Example 1 | Removal of NPA after separating water | 0.5 wt % | 99.995 | 2 | 10 | 0.995 | 1.11 |
| Example 2 | Removal of NPA after separating water | 5 wt % | 99.995 | 2 | 10 | 0.96 | 1.37 |
| Example 3 | Removal of NPA after separating water | 10 wt % | 99.995 | 2 | 10 | 0.88 | 1.88 |

[1] Chemical oxygen demand (COD) of water discharged from the lower portion of the first column, represented after normalization based on COD measured in Comparative Example 1.
[2] Amount of steam used throughout the purification process, represented after normalization based on the amount of steam used in Comparative Example 1.

In the above Table 1, in Comparative Example 1, NPA was first removed to the lower portion of the third column connected to the side of the first column in the IPA purification, but since an azeotropic mixture of IPA and NPA was formed by water included in the first column and the third column, NPA was included in the stream transferred to the second column, whereby 500 ppm of NPA and 250 ppm of water remained when final IPA was recovered to the lower portion of the second column. In addition, since high-boiling point organic substances (heavy substances) were included in water discharged to the lower portion of the first column, from the high-boiling point organic substances and then refluxed, thereby lowering the COD of water remaining in the lower stream of the first column. That is, since the content of the high-boiling point organic substances discharged to the lower stream 3*b* of the third column was proportional to the flow rate of the branch stream of the lower stream of the first column supplied to the first area of the third column, the COD of water remaining in the lower stream of the first column was lowered as a result.

Meanwhile, in Example 3, since the flow rate of the branch stream of the lower branch stream 1*b*' of the first column was increased to 10 wt %, it was shown that the amount of steam used by branch was rapidly increased. Therefore, in the branching of the lower stream of the first column, in order to lower the COD content of wastewater and avoid excessive energy consumption, it is preferred to adjust the flow rate of the branch stream to a predetermined range (for example, 0.5 to 5 wt % of the total flow rate of the lower stream of the first column).

The invention claimed is:

1. A method of preparing isopropyl alcohol (IPA), the method comprising:

(S1) performing gas purification to separate gas from a reaction product of a propylene monomer and water to obtain a feed stream including isopropyl alcohol (IPA), normal propyl alcohol (NPA), water, and high-boiling point organic substances; and (S2) supplying the feed stream to a purification unit including a plurality of columns to recover IPA, wherein, in a first column of the purification unit, the feed stream is separated into an upper stream including a mixture of IPA, NPA, and water and a lower stream including water and high-boiling point organic substances, wherein, in a second column of the purification unit, water is removed from the upper stream of the first column using an organic solvent, a stream including IPA and NPA is separated to a lower portion, and the organic solvent forms a three-component azeotropic mixture with water and IPA, which is discharged as an upper stream, and wherein a third column of the purification unit includes first and second areas which are separated by a center dividing wall, a mixed stream of a branch stream of the lower stream of the first column and the lower stream of the second column is supplied to the first area, where the mixed stream is separated into an upper stream including water from which the high-boiling point organic substances have been removed, a side stream including IPA from which NPA has been removed, and a lower stream including the high-boiling point organic substances and NPA, and the side stream including IPA is recovered from the second area.

2. The method of preparing IPA of claim 1, wherein the upper stream including the three-component azeotropic mixture of the organic solvent, water, and the IPA separated from the upper portion of the second column is transferred to a fourth column of the purification unit and separated into an upper stream from which water has been removed and a lower stream including water, and the upper stream is refluxed to the second column.

3. The method of preparing IPA of claim 1, wherein the feed stream includes 5 to 10 wt % of IPA, 0.1 to 3 wt % of NPA, 85 to 94 wt % of water, and 0.05 to 2 wt % of high-boiling point organic substances.

4. The method of preparing IPA of claim 1, wherein the upper stream from the first column includes a mixture of 30 to 70 wt % of IPA, 20 to 50 wt % of NPA, and 10 to 50 wt % of water.

5. The method of preparing IPA of claim 1, wherein a flow rate of the branch stream of the lower stream of the first column being supplied to the first area of the third column is adjusted to 0.5 to 5 wt % of the total flow rate of the lower stream of the first column.

6. The method of preparing IPA of claim 1, wherein a content of the high-boiling point organic substances separated into the lower stream of the third column is proportional to a flow rate of the branch stream of the lower stream of the first column being supplied to the first area of the third column.

7. The method of preparing IPA of claim 1, wherein IPA recovered from the second area in the third column satisfies a purity of 99.99 wt % or more.

8. The method of preparing IPA of claim 1, wherein the high-boiling point organic substances include hexanol.

9. The method of preparing IPA of claim 1, wherein the organic solvent used in the second column is selected from cyclohexane, benzene, toluene, and isopropyl acetate.

* * * * *